(12) United States Patent
Orczy-Timko et al.

(10) Patent No.: US 10,004,556 B2
(45) Date of Patent: Jun. 26, 2018

(54) TISSUE RESECTING DEVICES AND METHODS

(71) Applicant: ARQOS Surgical, Inc., Cupertino, CA (US)

(72) Inventors: Benedek Orczy-Timko, Budapest (HU); Csaba Truckai, Saratoga, CA (US); Aaron Germain, San Jose, CA (US)

(73) Assignee: Corinth MedTech, Inc., Cupertino, CA (US)

( * ) Notice: Subject to any disclaimer, the term of this patent is extended or adjusted under 35 U.S.C. 154(b) by 664 days.

(21) Appl. No.: 14/275,603

(22) Filed: May 12, 2014

(65) Prior Publication Data

US 2014/0336643 A1 Nov. 13, 2014

Related U.S. Application Data

(60) Provisional application No. 61/821,936, filed on May 10, 2013.

(51) Int. Cl.
*A61B 18/14* (2006.01)
*A61B 18/00* (2006.01)
(Continued)

(52) U.S. Cl.
CPC ........ *A61B 18/1447* (2013.01); *A61B 18/148* (2013.01); *A61B 18/149* (2013.01); *A61B 2017/00526* (2013.01); *A61B 2018/00083* (2013.01); *A61B 2018/00136* (2013.01); *A61B 2018/00208* (2013.01);
(Continued)

(58) Field of Classification Search
CPC ........... A61B 2018/00202; A61B 2018/00208; A61B 2018/00601; A61B 2018/1497; A61B 17/320783; A61B 2017/320028; A61B 17/320016; A61B 18/149
See application file for complete search history.

(56) References Cited

U.S. PATENT DOCUMENTS 2,513,564 A 7/1950 Ingwersen
2,514,545 A 7/1950 Ingwersen
(Continued)

FOREIGN PATENT DOCUMENTS

| EP | 1034747 A1 | 9/2000 |
|---|---|---|
| WO | WO 00/53112 A2 | 9/2000 |
| WO | WO 00/62685 A1 | 10/2000 |
| WO | WO 00/53112 A3 | 12/2000 |

OTHER PUBLICATIONS

U.S. Appl. No. 13/369,983, filed Feb. 9, 2012, Truckai et al.
(Continued)

*Primary Examiner* — Ronald Hupczey, Jr.
(74) *Attorney, Agent, or Firm* — Wilson Sonsini Goodrich & Rosati

(57) ABSTRACT

A tissue-resecting probe includes an elongated outer sleeve extending about an axis to a distal housing having a first window for receiving tissue. An edge of the first window has a dielectric surface. A rotatable inner sleeve has a second window, and at least a portion of an edge of the second window provides a first polarity electrode. Rotation of the inner sleeve within the outer sleeve moves the probe between window-open and window-closed configurations to resect tissue.

8 Claims, 10 Drawing Sheets

(51) Int. Cl.
*A61B 17/00* (2006.01)
*A61B 90/00* (2016.01)

(52) U.S. Cl.
CPC ............ *A61B 2018/00601* (2013.01); *A61B 2018/00642* (2013.01); *A61B 2018/00875* (2013.01); *A61B 2090/064* (2016.02); *A61B 2218/002* (2013.01); *A61B 2218/007* (2013.01)

(56) References Cited

U.S. PATENT DOCUMENTS

| | | | |
|---|---|---|---|
| 2,625,625 A | 1/1953 | Ingwersen | |
| 2,689,895 A | 9/1954 | Ingwersen | |
| 3,336,525 A * | 8/1967 | Church | G01D 5/202 |
| | | | 323/363 |
| 3,611,023 A | 10/1971 | Souza, Jr. et al. | |
| 3,838,242 A | 9/1974 | Goucher | |
| 3,848,211 A | 11/1974 | Russell | |
| 3,868,614 A | 2/1975 | Riendeau | |
| 3,903,891 A | 9/1975 | Brayshaw | |
| 4,060,088 A | 11/1977 | Morrison, Jr. et al. | |
| 4,272,687 A | 6/1981 | Borkan | |
| 4,781,175 A | 11/1988 | McGreevy et al. | |
| 4,977,346 A | 12/1990 | Gibson et al. | |
| 5,012,495 A | 4/1991 | Munroe et al. | |
| 5,122,138 A | 6/1992 | Manwaring | |
| 5,207,675 A | 5/1993 | Canady | |
| 5,256,138 A | 10/1993 | Burek et al. | |
| 5,281,217 A | 1/1994 | Edwards et al. | |
| 5,449,356 A | 9/1995 | Walbrink et al. | |
| 5,618,293 A * | 4/1997 | Sample | A61B 17/32002 |
| | | | 606/170 |
| 5,669,907 A | 9/1997 | Platt, Jr. et al. | |
| 5,683,366 A | 11/1997 | Eggers et al. | |
| 5,720,745 A | 2/1998 | Farin et al. | |
| 5,776,092 A | 7/1998 | Farin et al. | |
| 5,849,010 A | 12/1998 | Wurzer et al. | |
| 5,860,970 A * | 1/1999 | Goddard | A61B 18/02 |
| | | | 606/23 |
| 5,873,855 A | 2/1999 | Eggers et al. | |
| 5,888,198 A | 3/1999 | Eggers et al. | |
| 5,891,095 A | 4/1999 | Eggers et al. | |
| 5,904,681 A * | 5/1999 | West, Jr. | A61B 18/1485 |
| | | | 604/22 |
| 5,964,752 A | 10/1999 | Stone | |
| 5,989,248 A | 11/1999 | Tu et al. | |
| 6,013,076 A | 1/2000 | Goble et al. | |
| 6,024,733 A | 2/2000 | Eggers et al. | |
| 6,032,674 A | 3/2000 | Eggers et al. | |
| 6,039,736 A | 3/2000 | Platt, Jr. | |
| 6,056,747 A | 5/2000 | Saadat et al. | |
| 6,066,134 A | 5/2000 | Eggers et al. | |
| 6,013,075 A | 7/2000 | Avramenko et al. | |
| 6,099,523 A | 8/2000 | Kim et al. | |
| 6,142,992 A | 11/2000 | Cheng et al. | |
| 6,149,620 A | 11/2000 | Baker et al. | |
| 6,159,208 A | 12/2000 | Hovda et al. | |
| 6,193,715 B1 * | 2/2001 | Wrublewski | A61B 18/1402 |
| | | | 604/22 |
| 6,225,883 B1 | 5/2001 | Wellner et al. | |
| 6,235,020 B1 | 5/2001 | Cheng et al. | |
| 6,238,391 B1 | 5/2001 | Olsen et al. | |
| 6,296,636 B1 | 10/2001 | Cheng et al. | |
| 6,348,051 B1 | 2/2002 | Farin et al. | |
| 6,394,956 B1 | 5/2002 | Chandrasekaran et al. | |
| 6,413,256 B1 | 7/2002 | Truckai et al. | |
| 6,419,674 B1 | 7/2002 | Bowser et al. | |
| 6,443,948 B1 | 9/2002 | Suslov | |
| 6,471,712 B2 * | 10/2002 | Burres | A45D 29/14 |
| | | | 606/131 |
| 6,475,215 B1 | 11/2002 | Tanrisever | |
| 6,538,549 B1 | 3/2003 | Renne et al. | |
| 6,579,289 B2 | 6/2003 | Schnitzler | |
| 6,610,059 B1 * | 8/2003 | West, Jr. | A61B 17/32002 |
| | | | 606/41 |
| 6,632,220 B1 | 10/2003 | Eggers | |
| 6,635,034 B1 * | 10/2003 | Cosmescu | A61B 18/14 |
| | | | 601/35 |
| 6,669,694 B2 | 12/2003 | Shadduck | |
| 6,720,856 B1 | 4/2004 | Pellon et al. | |
| 6,780,178 B2 | 8/2004 | Palanker et al. | |
| 6,821,275 B2 | 11/2004 | Truckai et al. | |
| 6,837,884 B2 | 1/2005 | Woloszko | |
| 6,890,332 B2 | 5/2005 | Truckai et al. | |
| 6,902,564 B2 | 6/2005 | Morgan et al. | |
| 7,087,054 B2 | 8/2006 | Truckai et al. | |
| 7,220,261 B2 | 5/2007 | Truckai et al. | |
| 7,247,161 B2 * | 7/2007 | Johnston | A61B 17/162 |
| | | | 604/22 |
| 7,309,849 B2 | 12/2007 | Truckai et al. | |
| 7,549,989 B2 | 6/2009 | Morgan et al. | |
| 7,713,269 B2 | 5/2010 | Auge, II et al. | |
| 7,744,595 B2 | 6/2010 | Truckai et al. | |
| 7,771,422 B2 | 8/2010 | Auge, II et al. | |
| 7,819,861 B2 | 10/2010 | Auge, II et al. | |
| 7,819,864 B2 | 10/2010 | Morgan et al. | |
| 7,955,331 B2 | 6/2011 | Truckai et al. | |
| 8,016,823 B2 | 9/2011 | Shadduck | |
| 8,075,555 B2 | 12/2011 | Truckai et al. | |
| 8,192,424 B2 | 6/2012 | Woloszko | |
| 8,192,428 B2 | 6/2012 | Truckai et al. | |
| 8,221,404 B2 | 7/2012 | Truckai | |
| 8,323,280 B2 | 12/2012 | Germain et al. | |
| 8,333,763 B2 | 12/2012 | Truckai et al. | |
| 8,568,418 B2 * | 10/2013 | Matusaitis | A61B 17/32002 |
| | | | 606/180 |
| 2003/0014051 A1 | 1/2003 | Woloszko | |
| 2003/0060862 A1 * | 3/2003 | Goble | A61B 17/32002 |
| | | | 607/96 |
| 2003/0125727 A1 | 7/2003 | Truckai et al. | |
| 2004/0044341 A1 | 3/2004 | Truckai et al. | |
| 2005/0075630 A1 | 4/2005 | Truckai et al. | |
| 2005/0228372 A1 | 10/2005 | Truckai et al. | |
| 2006/0058782 A1 | 3/2006 | Truckai et al. | |
| 2006/0178670 A1 * | 8/2006 | Woloszko | A61B 18/1402 |
| | | | 606/48 |
| 2006/0200123 A1 * | 9/2006 | Ryan | A61B 18/148 |
| | | | 606/48 |
| 2006/0224154 A1 | 10/2006 | Shadduck et al. | |
| 2006/0264927 A1 * | 11/2006 | Ryan | A61B 17/32002 |
| | | | 606/45 |
| 2007/0213704 A1 | 9/2007 | Truckai et al. | |
| 2009/0076498 A1 | 3/2009 | Saadat et al. | |
| 2009/0093806 A1 * | 4/2009 | Govari | A61B 5/06 |
| | | | 606/34 |
| 2009/0270849 A1 | 10/2009 | Truckai et al. | |
| 2010/0100091 A1 | 4/2010 | Truckai | |
| 2010/0305565 A1 | 12/2010 | Truckai et al. | |
| 2012/0245580 A1 | 9/2012 | Germain et al. | |
| 2012/0330292 A1 * | 12/2012 | Shadduck | A61B 18/18 |
| | | | 606/13 |
| 2013/0090642 A1 | 4/2013 | Shadduck et al. | |
| 2013/0296847 A1 * | 11/2013 | Germain | A61B 50/13 |
| | | | 606/39 |
| 2013/0296849 A1 | 11/2013 | Germain et al. | |
| 2013/0317493 A1 | 11/2013 | Truckai et al. | |
| 2013/0331833 A1 * | 12/2013 | Bloom | A61B 18/1445 |
| | | | 606/33 |
| 2013/0345704 A1 * | 12/2013 | Palmer | A61B 18/148 |
| | | | 606/46 |
| 2014/0100567 A1 * | 4/2014 | Edwards | A61B 17/32002 |
| | | | 606/42 |
| 2014/0303611 A1 * | 10/2014 | Shadduck | A61B 18/148 |
| | | | 606/33 |

OTHER PUBLICATIONS

European search report dated Nov. 2, 2009 for EP Application No. 01967968.7.

International search report dated Jan. 14, 2002 for PCT/US2001/025409.

(56) References Cited

OTHER PUBLICATIONS

International search report and written opinion dated May 23, 2012 for PCT/US2012/023390.
Tucker et al. Histologic characteristics of electrosurgical injuries. J. Am. Assoc. Gyneco. Laproscopy. 1997; 4(2):857-862.
Kim, et al. Optical feedbacksignal for ultra short pulse ablation of tissue. Appl. Surface Sci. 1998; 127-129:857-862.

\* cited by examiner

ND METHODS

CROSS-REFERENCE TO RELATED APPLICATIONS

This application claims the benefit of U.S. Provisional Application No. 61/821,936, filed May 10, 2013, the entire content of which is incorporated herein by reference.

BACKGROUND OF THE INVENTION

1. Field of the Invention

The present invention relates to systems and methods for resecting and extracting tissue in arthroscopy and other fields.

Electrosurgical cutting devices often comprise a shaft or sleeve having a tissue extraction lumen with one or more radio frequency (RF) cutting blades arranged to resect tissue which may then be drawn into the extraction lumen, often via vacuum assistance. Most such electrosurgical tissue cutting devices rely on manually engaging the electrode or other tissue-cutting edge against the target tissue to be resected. While such manual engagement is often sufficient, in other cases, such as in laparoscopic procedures having limited access, the target tissue can be difficult to immobilize prior to resection. For these reasons, it would be desirable to provide improved electrosurgical cutting tools having the ability to engage and immobilize tissue prior to cutting.

2. Description of the Background Art

Related patents and applications include U.S. Pat. No. 8,221,404; U.S. Pat. No. 7,744,595; U.S. 2010/0305565; U.S. 2007/0213704; U.S. 2009/0270849; and U.S. 2013/0090642.

SUMMARY OF THE INVENTION

In a first aspect of the present invention, a tissue-resecting probe comprises an elongated outer sleeve extending about an axis to a distal housing having a first window for receiving tissue. An edge of the first window has a dielectric surface. A rotatable inner sleeve has a second window wherein at least a portion of an edge of the second window comprises a first polarity electrode and wherein rotation of the inner sleeve within the outer sleeve moves the probe between window-open and window-closed configurations to resect tissue.

The edge of the second window usually includes a plurality of openings and bridges between the first polarity electrode, and a portion of the inner sleeve that has dielectric surfaces. A proximal edge of the second window typically has a dielectric surface, and a lateral edge of the second window comprises the first polarity electrode. In some embodiments, both lateral edges of the second window comprise the first polarity electrode.

In other embodiments, a lateral edge of the second window has a dielectric surface, and a distal edge of the second window may at least partly comprise the first polarity electrode. In still other specific embodiments, the first polarity electrode is symmetric about the second window relative to said axis, and in still other embodiments, the first polarity electrode is asymmetric about the second window relative to said axis. In still further specific aspects, the edge of the second window includes a plurality of openings and bridges between the first polarity electrode and a portion of the inner sleeve having dielectric surfaces, wherein the cumulative length of the openings parallel to the edge of the second window is typically at least 50% of the length of said first polarity electrode about the edge of the second window.

Further optionally, a portion of the outer sleeve may comprise a second polarity electrode, and a negative pressure source may be placed in communication with an interior passageway in the inner sleeve.

In a second aspect of the present invention, a tissue-resecting probe comprises an elongated probe including a windowed outer sleeve and cooperating windowed inner sleeve that is rotatable to resect tissue. An edge of the inner sleeve window comprises a first polarity electrode and a portion of the outer sleeve comprises a second polarity electrode. A controller and electrical source are operatively connected to the first and second electrodes, and the controller is configured to activate the electrodes only during part of each 360° rotation of the inner sleeve.

The controller is usually configured to activate the electrodes during 90° to 180° rotation of each 360° rotation of the inner sleeve. Optionally, the controller is configured to activate the electrodes only when an advancing edge of the inner sleeve window is exposed in the outer sleeve window. In such embodiments, a microswitch is configured for actuation during each 360° rotation of the inner sleeve, wherein the controller activates and de-activates the electrodes in response to signals from the microswitch, and the controller optionally activates and de-activates the electrodes in response to a measured electrical parameter, typically impedance, relative to electrodes that varies during each 360° rotation of the inner sleeve.

In a third aspect of the present invention, a tissue-resecting probe comprises an elongated probe having a windowed outer sleeve and a cooperating windowed inner sleeve that is rotatable to resect tissue. An edge of the inner sleeve window comprises a first polarity electrode and a portion of the outer sleeve comprises a second polarity electrode. A controller and electrical source are operatively connected to the first and second electrodes, and the controller is configured to receive user inputs to stop the inner sleeve rotationally relative to the outer sleeve in at least first and second positions.

In said first position, the tissue-resecting probe aligns the outer and inner sleeve windows to provide an open window configuration. In said second position, the outer and inner sleeve windows are not aligned, providing a partly open window configuration.

A microswitch is configured for actuation during each 360° rotation of the inner sleeve, and the controller includes an algorithm to stop the inner sleeve rotationally in the first or second positions in response to a signal from the microswitch. The controller includes an algorithm to stop the inner sleeve rotationally in the first or second positions in response to a measured electrical parameter, typically impedance, relative to electrodes that varies during each 360° rotation of the inner sleeve.

In a fourth aspect of the present invention, a tissue-resecting probe comprises an elongated probe including a windowed outer sleeve and a cooperating windowed inner sleeve that is rotatable to resect tissue, wherein an edge of the inner sleeve window comprises a first polarity electrode and a portion of the outer sleeve comprises a second polarity electrode. A motor probe for rotating the inner sleeve is disposed within a handle, and a slip couples between a motor shaft and the inner sleeve. The slip may comprise at least one belt and acts as a clutch which slips if resistance to rotation of the inner sleeve exceeds a predetermined level. A controller and electrical source may be provided for operating the motor and for energizing the electrodes. An exemplary controller operates with an algorithm for detecting electrical parameters of the motor indicative of slipping of the slip coupling.

The algorithm may be further configured to de-energize the electrodes upon detection of slipping of the slip coupling.

In a fifth aspect, a method for fabricating an electrosurgical component including an electrically conductive core covered by thin polymeric insulating coating comprises providing a metal core having an external metal surface. A plurality of adherence features are created over at least a portion of the external metal surface, wherein the adherence features include undercuts. A polymeric insulating layer is formed over the external surface wherein the polymer extends beneath the undercuts to enhance adherence of the polymeric insulating layer to the external metal surface.

The creating step typically includes at least one of metal or ceramic sputtering, metal spraying, and electroless plating under conditions selected to apply discrete metal features and not apply a continuous metal film. Optionally, the creating step may also include drilling, e.g. laser drilling, to provide the undercut features. Alternatively, the creating step may include at least one of sandblasting and burnishing. Usually, the metal core is formed at least partially from stainless steel, and the polymeric insulating layer is composed at least partially of a FEP (fluorinated ethylene propylene) or a PFA (perfluoroalkoxy). The polymeric insulating layer is often formed to have a thickness in the range of 0.001 inch to 0.05 inch.

In a sixth aspect of the present invention, a tissue-resecting probe comprises an elongated probe comprising a windowed outer sleeve and cooperating windowed inner sleeve that is rotatable to resect tissue, wherein an edge of the inner sleeve window comprises a first polarity electrode and a portion of the outer sleeve comprises a second polarity electrode. A controller is configured to control a negative pressure source in communication with a passageway in the inner sleeve, wherein the controller is configured to activate the negative pressure source only during part of each 360° rotation of the inner sleeve.

The controller is typically configured to activate the negative pressure source during 30° to 180° rotation of each 360° rotation of the inner sleeve.

In a seventh aspect of the present invention, a tissue-resecting probe comprises an elongated probe having a working end with a windowed outer sleeve and cooperating windowed inner sleeve that is rotatable to resect tissue, wherein an edge of the inner sleeve window comprises a first polarity electrode and a portion of the outer sleeve comprises a second polarity electrode. At least one port is formed in the outer sleeve of the working end, and a moveable member has a first position that permits fluid flow through the at least one port and a second position that prevents fluid flow through the at least one port.

The outer sleeve usually has a plurality of ports and the moveable member is moveable between a plurality of positions to permit fluid flow through one or more ports.

In an eighth aspect of the present invention, a tissue-resecting probe comprises an elongated probe including a windowed outer sleeve and a cooperating windowed inner sleeve that is rotatable to resect tissue. An edge of the inner sleeve window comprises a first polarity electrode and a portion of the outer sleeve comprises a second polarity electrode. A motor is attached to move the inner sleeve, and an electrical source is operatively connected to the first and second electrodes. A pressure source is in communication with a passageway in the inner sleeve, and a controller controls the motor, the electrical source and the pressure source, and the controller is configured to selectively provide negative pressure or positive pressure to the interior passageway.

The controller is usually configured to receive user input to select negative pressure or positive pressure. For example, the controller may be configured to receive a signal of an operational parameter of the motor to select negative pressure or positive pressure. Alternatively, the controller may be configured to receive a pressure signal from a pressure sensor to select negative pressure or positive pressure. The controller could also be configured to de-activate the first and second electrodes in response to a signal of an operational parameter of the motor or be configured to de-activate the first and second electrodes in response to a pressure signal from a pressure sensor. As another option, the controller may be configured to de-activate the first and second electrodes in response to selection of a negative pressure or positive pressure applied to the interior passageway.

In a ninth aspect of the present invention, a tissue-resecting probe comprises an elongated outer sleeve extending about an axis to a distal housing having a first window for receiving tissue. An edge of the first window has a dielectric surface, and a rotatable inner sleeve has a second window wherein at least a portion of an edge of the second window comprises a first polarity electrode having a surface area of less than 0.02 sq. in., less than 0.01 sq. in. or less than 0.005 sq. in.

DETAILED DESCRIPTION OF THE INVENTION

Figure 1:
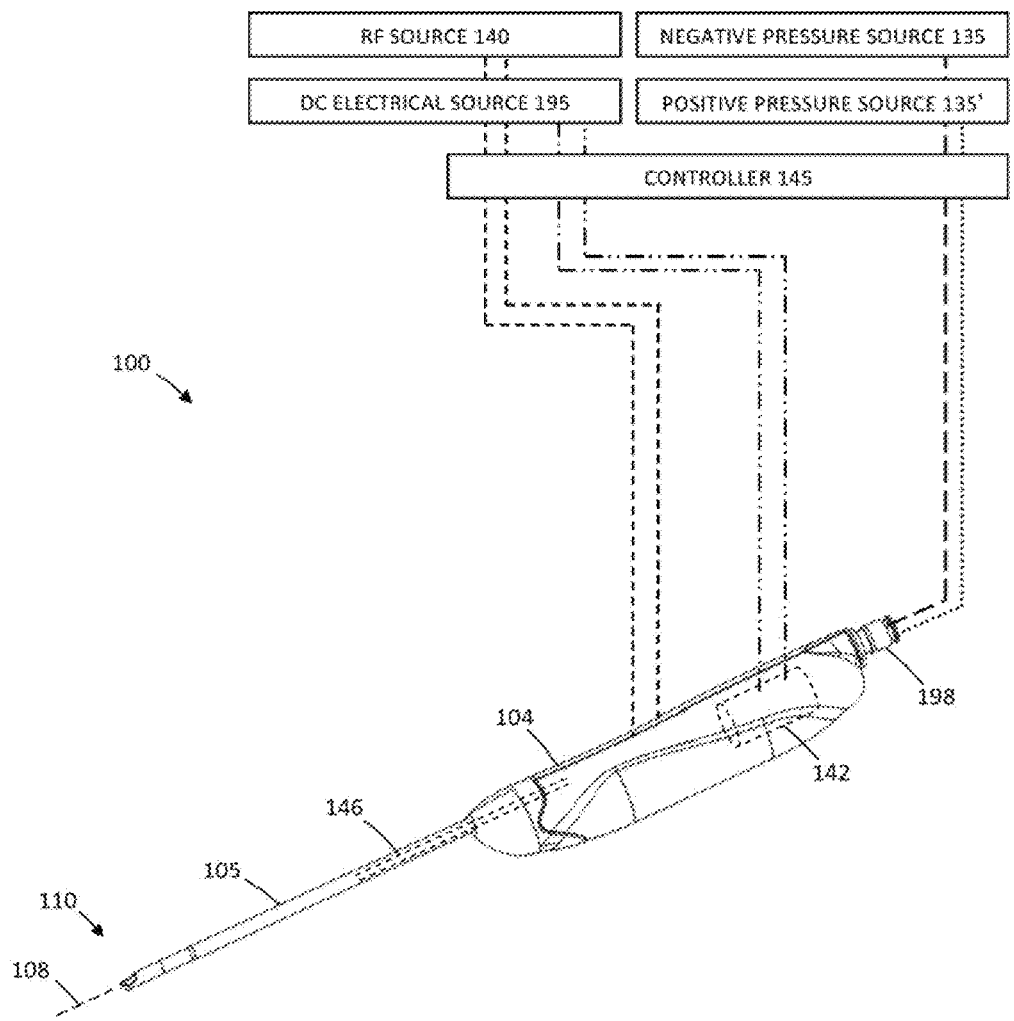
FIG. 1 is a perspective view of an electrosurgical resecting probe corresponding to the invention.

FIG. 1 illustrates an electrosurgical tissue resecting probe or tissue extraction probe 100 having a handle portion 104 that is coupled to an extension portion or shaft 105 that can have a diameter of 3 mm to 10 mm. The extension portion 105 extends along axis 108 and can have a length suitable for introduction directly in a body space or introduction though a working channel of an endoscope. A probe corresponding to the invention as depicted in FIG. 1 is adapted for arthroscopy, but similar elongated probes can be used for resecting tissue in a male patient's prostate, in a female patient's uterus or in any other procedures in a body cavity or space under endoscopic viewing.

Figure 2A:
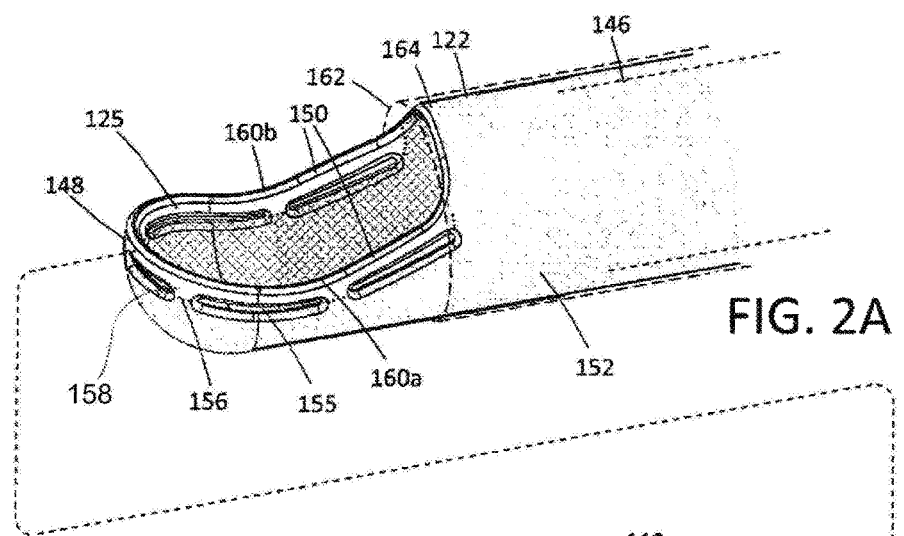
FIG. 2A is a perspective view of the working end of the inner sleeve of the resecting probe of FIG. 1.
Figure 2B:
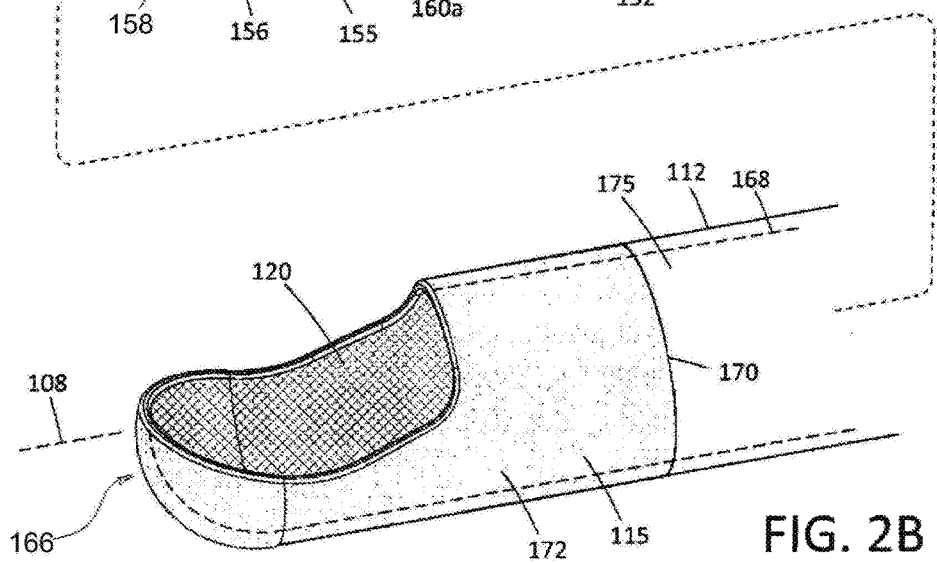
FIG. 2B is a perspective view of the working end of the outer sleeve of the resecting probe of FIG. 1.
Figure 3:
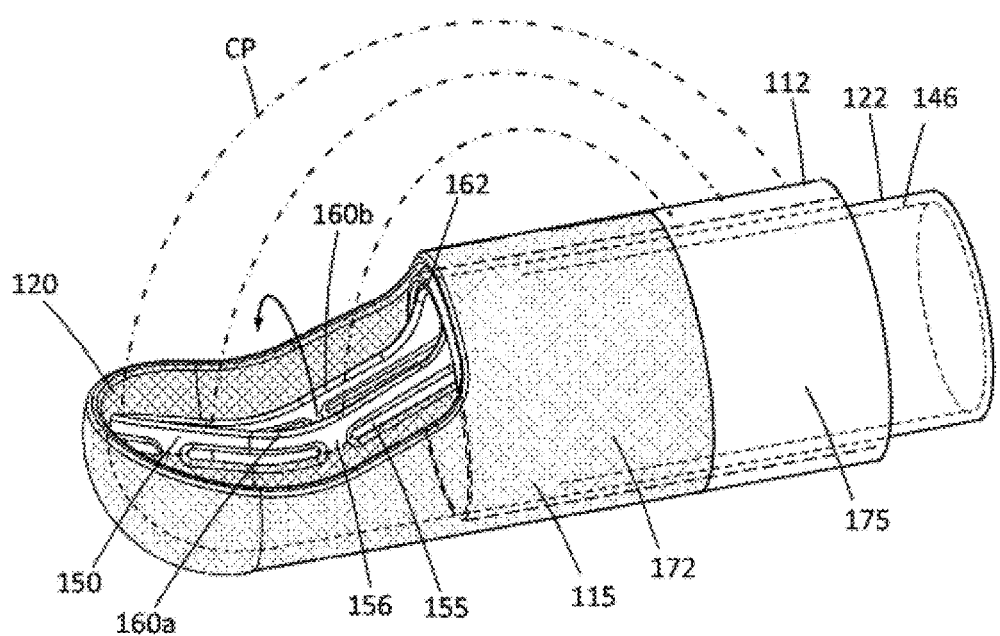
FIG. 3 is a view of the assembled inner and outer sleeves of FIGS. 2A and 2B showing an electrode arrangement and RF current paths when in use and immersed in a conductive fluid.

Referring to FIGS. 1, 2A-2B and 3, the tissue resecting probe 100 has a shaft 105 and working end 110 comprising an assembly of outer sleeve 112 (FIG. 2B) extending about axis 108 to a distal housing 115 having a first window 120 for receiving tissue and a rotatable inner sleeve 122 (FIG. 2A) that has a second window 125 that is dimensioned to cooperate with the first window 120 to receive and resect tissue. FIG. 3 shows the assembly of outer sleeve 112 and inner sleeve 122 with the inner sleeve rotating from a window-open position toward a window-closed position.

The tissue resecting probe 100 of FIGS. 1-3 includes subsystems operatively coupled handle 104 and an electrode arrangement carried by the working end 110 to enable electrosurgical resection and extraction of targeted tissue. A radiofrequency generator or RF source 140 and controller 145 are coupled to an electrode arrangement that is described in detail below. In one variation, a negative pressure source 135 is in fluid communication with a tissue extraction channel 146 in the inner sleeve 122 that rotates within the shaft 105. As will be described below, the inner sleeve 122 is rotatable by an electrical motor 142 in handle portion 104 (see FIG. 4). The controller 145 is adapted to control operational parameters of all subsystems, including energizing the electrode arrangement, actuating the motor 142 to rotate the inner sleeve 122 and activating the negative pressure source 135 and an optional positive pressure source 135'.

Referring now to FIGS. 2A and 2B, the distal ends of inner sleeve 122 and outer sleeve 112 are shown de-mated from one another to better describe the electrode arrangement. In FIG. 2A, one variation of inner sleeve 122 can comprise a thin-wall electrically conductive stainless steel tube with rounded end 148 and window 125 therein. A connector 149 in handle 104 couples a first pole of the RF source 140 with a spring contact that engages the proximal end 136 of inner sleeve 122. A portion of the edge of the inner sleeve window 125 comprises a first polarity electrode 150. As can be seen in FIG. 2A, the edge of window 125 is bare stainless steel to thus function as first polarity electrode 150. In FIG. 2A, it can be seen that the exterior and interior of sleeve 122, except for the edge of window 125, has a thin electrically insulating coating or dielectric surface 152 (indicated by cross-hatched area), which can be any suitable material such as Teflon. A method of fabricating the thin insulating coating 152 is provided below. In one variation shown in FIG. 2A, the window edge includes a plurality of openings 155 and bridges 156 between the first polarity electrode 150 and a portion of the inner sleeve that has a dielectric surface 152. The openings 155 and bridges 156 function to limit the exposure of the edges 158 of the dielectric surface 152 to plasma that forms about the electrode 150. The bridges 156 have a sufficient cross-section to carry current to the edge electrode 150 from the body of sleeve 122. The openings 155 can range in number from 1 to 100 and in one variation are between 2 and 6 and are elongated and extend substantially parallel to the edge of window edge 125. The width (measured radially) of the openings 155 in one variation shown in FIG. 2A is between 0.005" and 0.10". In one aspect of the invention, the opening or openings 155 have a cumulative length measured parallel to the edge of window 125 that is at least 50% of the length of said first polarity electrode 150 about the edge of window 125. The bridges 156 can be symmetrical relative to window 125 as shown in FIG. 2A or can be asymmetrical as will be described in another variation below. In some variations, the first polarity electrode 150 can extend along both lateral edges 160a and 160b of window 125 and in other variations, the first polarity electrode 150 can extend only along one lateral edge 160a of window 125. In FIG. 2A, an insulator sleeve 162 is shown in phantom view and extends distally over the proximal edge 164 of window 125 and extends proximally to handle portion 104. The insulator sleeve 160 can be any suitable material such as FEP heat shrink material and is adapted to provide a continuous insulator layer between the inner and outer sleeves, 22 and 112, within the elongate shaft 105. The insulator coating 152 in FIG. 2A can extend proximally about the inner surface of tissue extraction channel 146 of the inner sleeve 122 from 5 mm to 50 mm from the proximal edge 164 of window 125.

Now turning to FIG. 2B, the distal end of outer sleeve 112 is shown. One variation of outer sleeve 112 comprises a thin-wall electrically conductive stainless steel tube with housing 115 having a rounded end 166 and window 120 therein. The inner sleeve 122 rotates within bore 168 in outer sleeve 112. In one variation, the housing 115 is welded to outer sleeve 112 at joint 170 and the housing 115 is entirely coated (inside and outside) with a thin insulator layer or dielectric 172, such as Teflon, as described above with reference to inner sleeve 122. A connector 173 in handle 104 couples a second pole of the RF source 140 to a proximal end 174 of the outer sleeve 112. The second polarity electrode 175 thus comprises a distal portion of outer sleeve 112 proximal to the insulated housing 115 as shown in FIG. 2B.

In FIG. 3, the working end 110 is shown with the assembled inner sleeve 122 and outer sleeve 112 with the leading edge 160a of electrode 150 of the inner sleeve as it rotates from the window-open position. In use, for example in an arthroscopic procedure, the working end 110 would be submersed in conductive saline solution and would be in contact with targeted tissue and the current paths CP are indicated schematically between the first polarity electrode 150 and the second polarity electrode 175.

Figure 4:
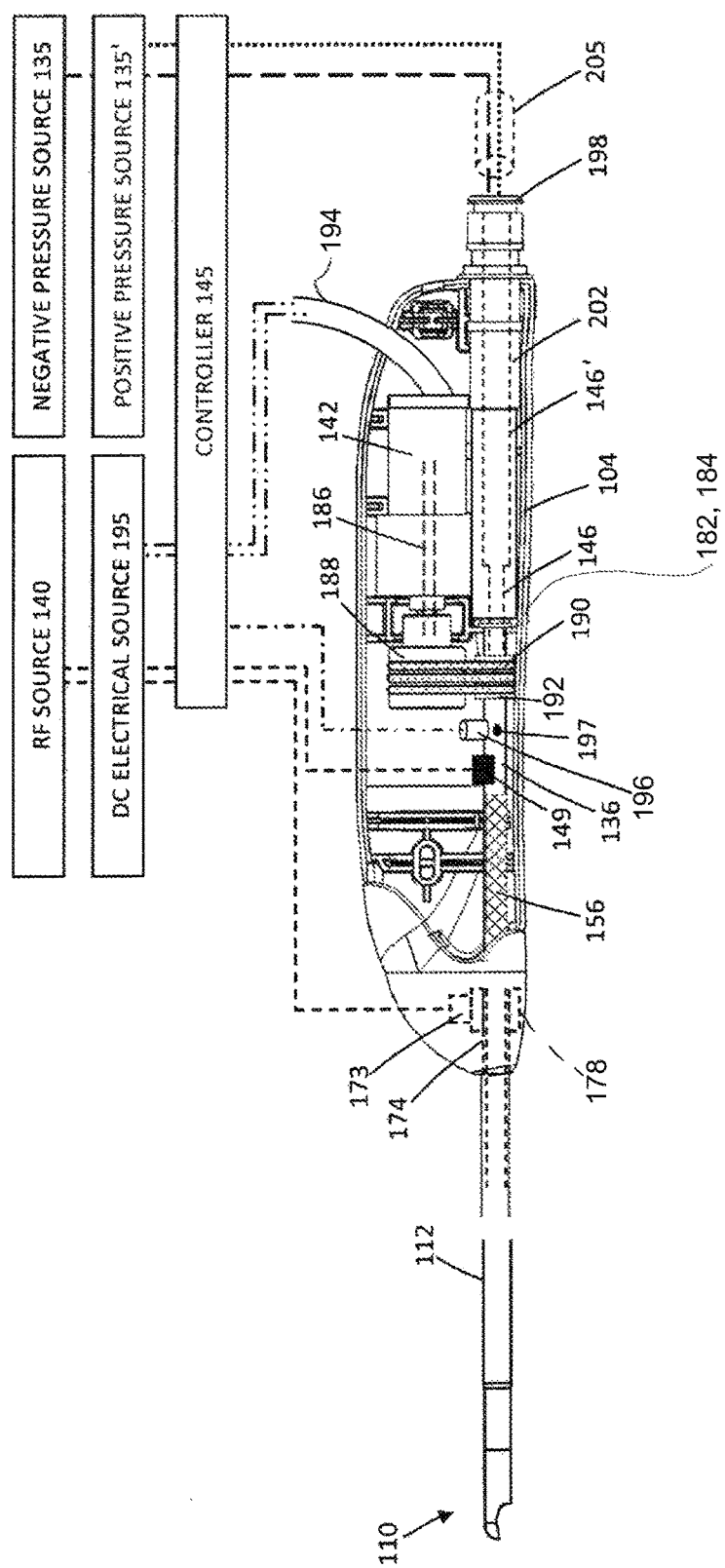
FIG. 4 is a cut-away view of the handle of the resecting probe of FIG. 1 with a block diagram of energy delivery and controller components of the system.

FIG. 4 is a cut-away view of handle 104 of the probe showing outer sleeve 112 fixed to collar 178 in the handle. The rotatable inner sleeve 122 extends partly through the interior of the handle 104 to a proximal sleeve end 182 that rotates in a bore in support bracket 184. The handle 104 typically can be a molded plastic two-part handle with a hollow interior.

An electric DC motor 142 is housed with the handle with motor shaft 186 having a pulley 188 that carries at least one flexible belt 190 for rotating the inner sleeve 122. The inner sleeve 122 has pulley 192 that engages the belts 190 which can be fabricated of rubber, Viton® or the like. The DC motor can be geared (together with pulleys 188 and 192) to drive the inner sleeve 122 at from 500 to 5000 rpm and in one embodiment is 900 rpm. The motor 142 an has electrical cable 194 extending therefrom to the controller 145 and a DC electrical source 195.

In one aspect of the invention, the at least one flexible belt 190 is adapted to slip in the event that rotation of inner sleeve 122 is met with excessive resistance during a procedure, for example which could occur when the inner sleeve 122 is resecting very dense tissue or when the inner sleeve 122 comes into contact with bone. In another variation, the controller 145 also can have an algorithm that continuously receives signals from a sensor mechanism that signals the controller of the actual rpm of the inner sleeve 122 during use, and the algorithm further can de-energize the electrode arrangement if rotation of the inner sleeve 122 stalls or slows to a predetermined low cut-off speed, such as below 100 rpm, 200 rpm, or 300 rpm. The algorithm can further provide for re-energizing the electrode arrangement if the inner sleeve 122 regains a predetermined rpm above the cut-off speed, which could occur when the physician moves or re-adjusts the working end relative to dense tissue or bone that had impeded rotation. In one embodiment, the sensor mechanism for determining rpm of the inner sleeve 122 comprises a microswitch 196 shown in FIG. 4 that hits a feature 197 (e.g., a detent or protrusion) on the proximal end 136 of inner sleeve 122. The controller 145 then can read the rpm of the inner sleeve 122 with use of its internal clock and the microswitch 196 that is actuated on each revolution of the inner sleeve 122. Other types of microswitches or sensors can be used such as optical sensors, Hall affect sensors and the like.

As can be seen in FIG. 4, the tissue extraction channel 146 in inner sleeve 122 extends through handle 104 to male quick-connect fitting 198. In one variation, the extraction channel 146 in sleeve 122 transitions to a larger cross-section channel 146' in body member 202 in handle 104. The larger cross-section allows for improved flow of fluid and tissue chips through the system. A flexible tubing 205 can be detachably coupled to quick-connect fitting 198 and can extend to the negative pressure source 135 such as wall suction in an operating room or to a peristaltic pump or other pump. As will be described further below, a positive pressure source 135' also may communicate with the tubing 205 for reversing the direction of fluid flow, for example, to remove a clog in the tissue extraction channel 146 of the probe.

Figure 5A:
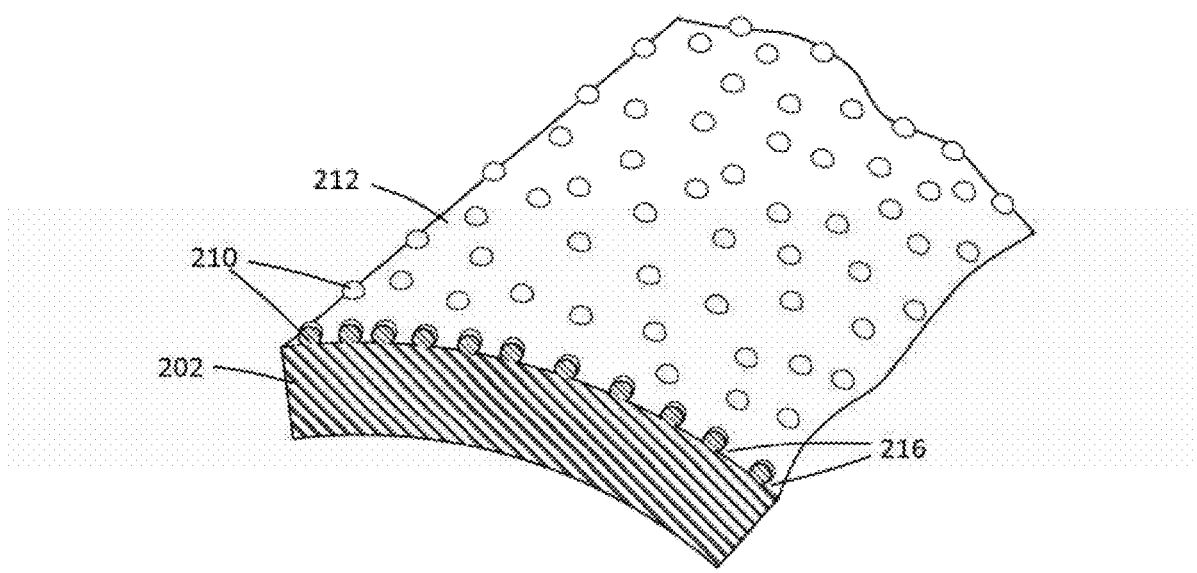
FIG. 5A is an enlarged view of a portion of a metal sleeve of the probe of FIG. 1 showing a first step in making a conductive electrode sleeve with a thin-wall dielectric material secured to an exterior of the sleeve, which includes sputtering metal on the sleeve to provide undercuts for adherence of a polymeric coating.
Figure 5B:
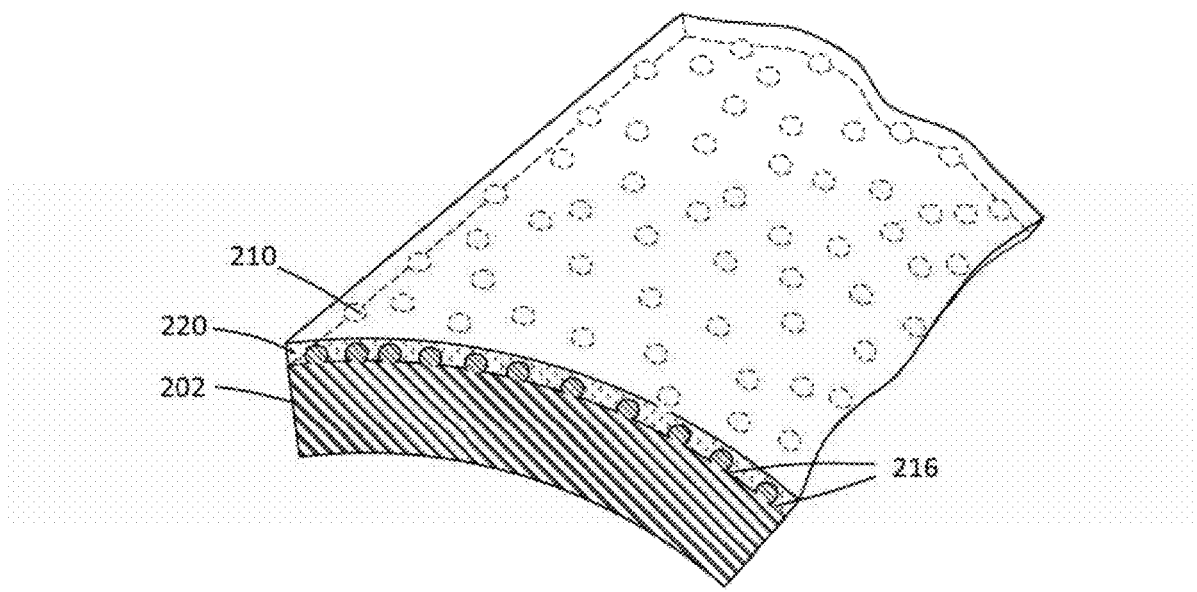
FIG. 5B shows the sleeve of FIG. 5A following a second step of depositing a thin layer of a polymer dielectric material such as Teflon on the sleeve.

Now turning to another aspect of the invention, FIGS. 5A-5B schematically illustrate a method of fabricating an electrically conductive metal component, such as inner sleeve 122 of the probe of FIGS. 1-4, with a thin insulative coating that is robustly secured to the metal structure. In many electrosurgical devices, it is useful to provide an elongated structural shaft component that also is used to carry RF energy to an electrode or electrode portion, but at the same time providing one or more surfaces of the component having a thin insulative coating or layer that cannot be easily detached, eroded or removed when an exposed portion of the component comprises an electrode. FIG. 5A shows a portion of a metal sleeve 202 (similar to sleeve 122 of FIGS. 1-4) which has metal droplet microstructure 210 (not to scale) deposited on the surface 212 of sleeve 202. The metal droplets 210 can be provided by a sputtering process as known in the art. In general, sputter deposition can be form of physical vapor deposition (PVD) which is typically used to deposit thin films on a substrate. In a method of the invention, the deposited material does not form a uniform thickness film over the entire surface of the metal, but is adapted to provide droplets and a microstructure that includes "undercuts" 216 which can be engaged by a second outer polymer layer 220 that is deposited on the sleeve 202. There are many process parameters in sputter deposition that can be adjusted to develop the microstructure on the surface of the metal, which generally is adapted to provide the undercut structure on a microscale to enhance attachment of the surface polymer layer. In the sputtering process, the high temperatures of the deposited materials will cause the microstructure to be fused to the metal surface (see FIG. 5A). FIG. 5B schematically shows the second step of the fabrication method in which a polymeric material 220 is deposited on the metal surface and droplet microstructure 210 to provide the insulator layer of any suitable thickness, for example from 0.001 to 0.050" or more. A suitable insulative material can be FEP (fluorinated ethylene propylene), PFA (perfluoroalkoxy), Parylene or similar materials. In another variation, the microstructure following vapor deposition can be mechanically treated or flattened to enhance the undercut characteristics of the microstructure. In another variation, metal spraying or electroless plating can be use to deposit an undercut microstructure on a sleeve surface to be followed by deposition of a polymer as described above. In general, the fabrication method comprises deposition or micromachining methods for creating an undercut microstructure as described above.

In another variation and method similar to that described with reference to FIGS. 5A-5B, a sputtering process as known in the art can be used to deposit a ceramic material, such as zirconium dioxide or aluminum oxide, on the surface of metal component 202 (FIG. 5A). The ceramic material may or may not comprise a layer over the entire surface of the metal component 202 (cf. FIG. 5A) but in any event provide an adherent surface with undercuts 216 (FIG. 5B) for permitting a polymer material 220 to grip the surface. The ceramic "undercut" layer provides an advantage in that the polymeric material 220 may be scratched of scraped in an arthroscopic procedure, for example by contact with bone. In such a case when the insulative polymeric layer is damaged, there would remain a strong ceramic layer under the polymeric layer and the damage typically could not extend through to the metal component 202 (FIG. 5B). The ceramic "undercut" layer thus would prevent an unwanted RF current path through any damaged region of the polymeric material 220 to the underlying metal component 202.

Figure 6A:
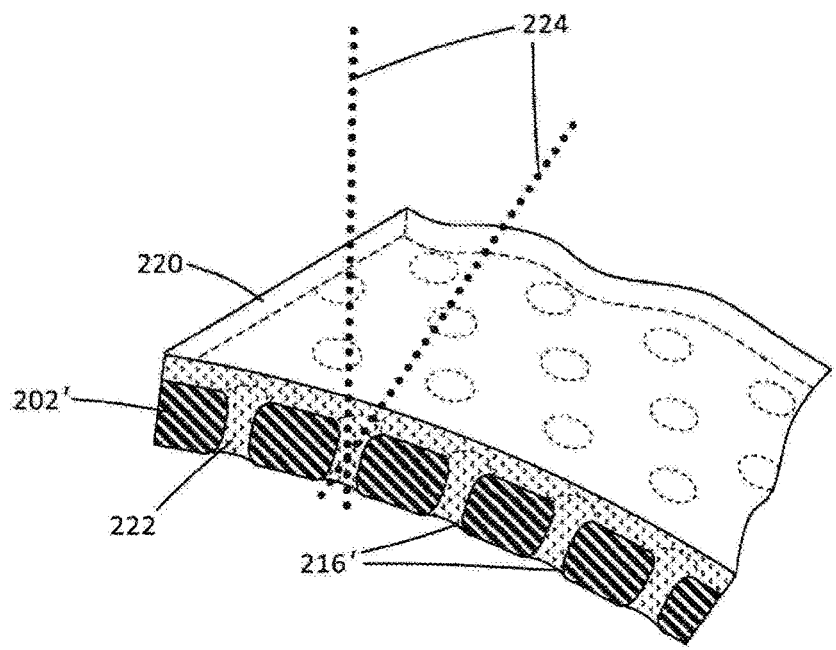
FIG. 6A is an enlarged view of a metal sleeve similar to that of FIG. 5A showing a method using a laser to drill through holes to provide undercuts for adherence of a polymeric coating.
Figure 6B:
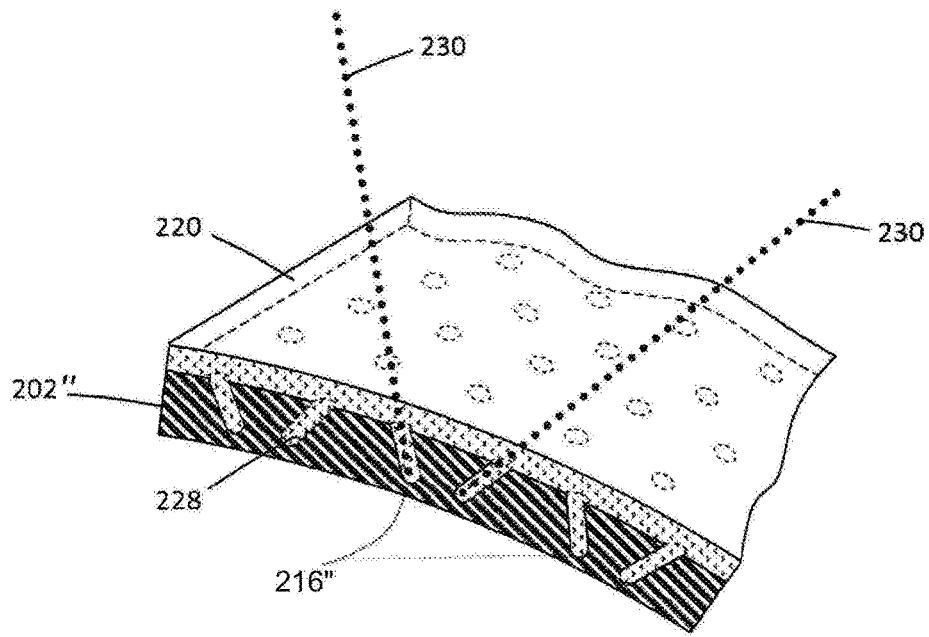
FIG. 6B is a view of a metal sleeve similar to that of FIG. 6A showing a method using a laser to drill angled holes to provide an undercut surface for adherence of a polymeric coating.

FIGS. 6A-6B schematically illustrate other variations of providing an undercut structure which allows for a polymeric layer 220 to adhere to a metal component. FIG. 6A shows metal component 202' with undercuts 216' consisting of bell-shaped holes 222 drilled by laser machining as laser beams 224 can be angled to provide the undercuts 216'. It can be seen in FIG. 6A that the polymeric layer 220 would be anchored in holes 222 and be resistant to detachment. FIG. 6B shows another variation in which metal component 202" has undercuts 216" with a plurality of angled bores 228 drilled by laser beams 230 to provide the undercuts 216". The methods depicted in FIGS. 5A-6B can be used to fabricate insulative surface layers on both sleeves 112 and 122 in the probe of FIGS. 1-4.

Figure 7:
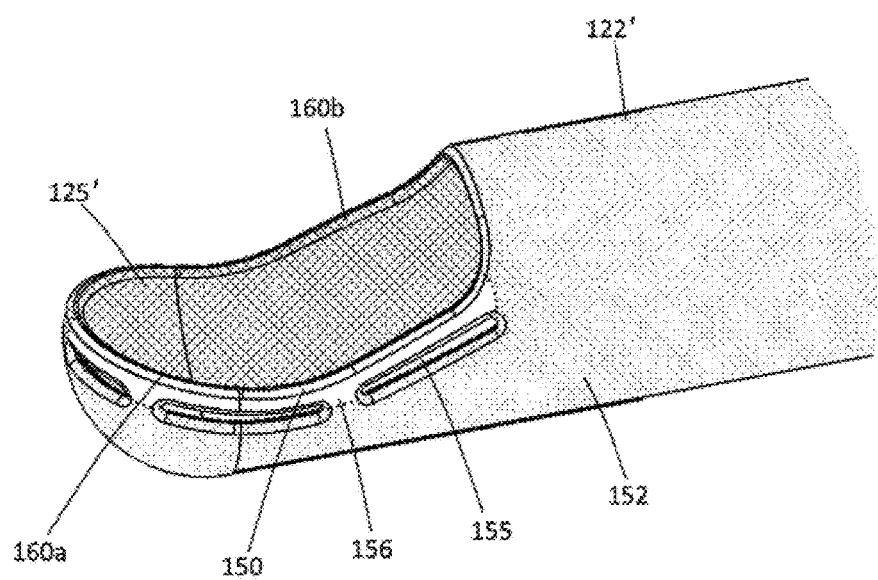
FIG. 7 is a perspective view of the working end of another variation of an inner sleeve which is configured with an asymmetric electrode.

Now turning to FIG. 7, the distal end of a variation of inner sleeve 122' is shown. The variation of inner sleeve 122' includes an asymmetric electrode configuration that can be used with the same outer sleeve as depicted in FIG. 2B. The distal end of inner sleeve 122' of FIG. 7 differs in only the leading edge 160a of window 125' comprises an electrode 150. The leading edge 160a is the edge that contacts tissue during rotation while the trailing edge 160b only passes over the already cut tissue chip. In this variation, all RF current thus is passed through the electrode 150 at the leading edge 160a. In all other respects, the working end of a probe using the asymmetric first electrode 150 of inner sleeve 122' would function as described previously.

Figure 8A:
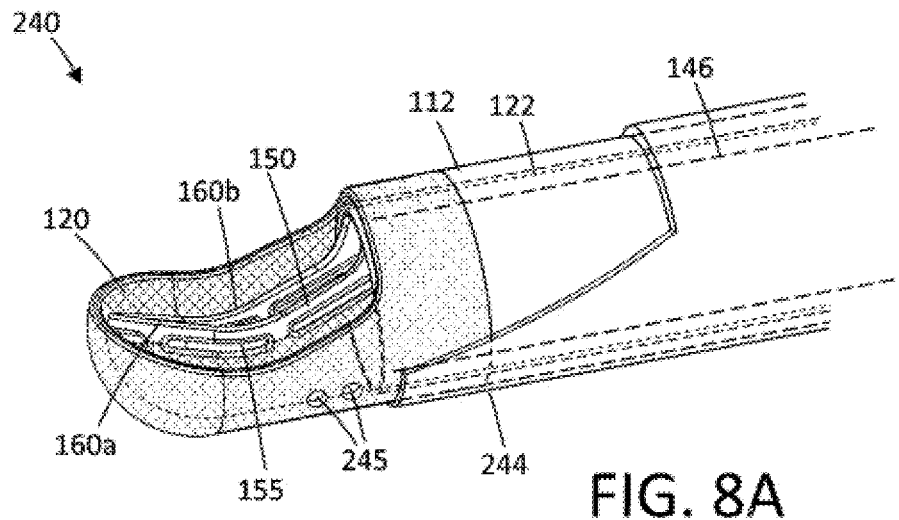
FIG. 8A is a perspective view of the working end of an alternative resecting probe with a moveable exterior sleeve in a first position relative to through holes in the working end.
Figure 8B:
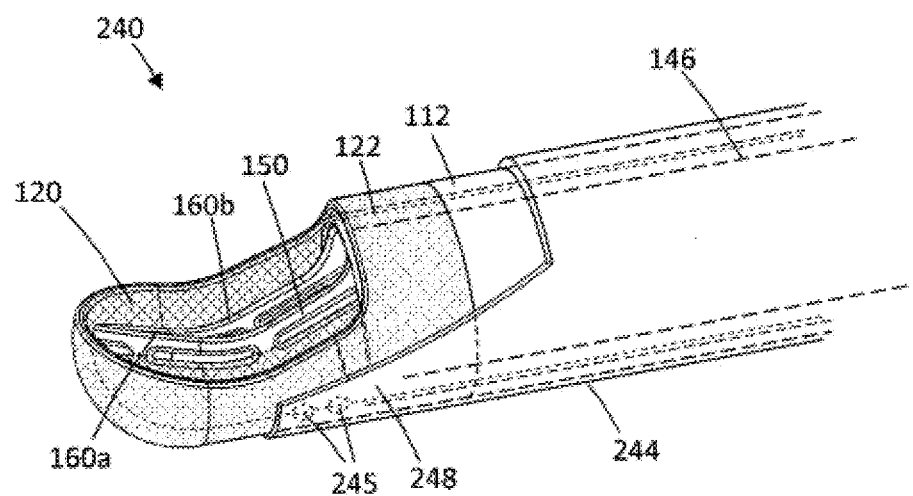
FIG. 8B is a view of the working end of FIG. 8A with the exterior sleeve in a second position to cover the through holes in the working end.

FIGS. 8A-8B illustrate another variation of working end 240 that is similar to the probe of FIGS. 1-4. This variation includes an additional feature that comprises an axially sliding sleeve 244 that can be moved by the physician to cover or uncover through holes 245 in the outer sleeve 112 of the working end. In FIG. 8A, it can be seen that holes 245 are not covered and in FIG. 8B, the holes 245 are covered by distal portion 248 of sleeve 244. It can be understood that when the inner sleeve 122 is rotated to a window-closed position, then irrigation fluid can flow through to holes 245 and thereafter through extraction channel 146 of the probe under the influence of negative pressure source 135 (see FIGS. 1 and 4). With holes 245 open as in FIG. 8A, the fluid flows through the probe may be enhanced to assist is extracting tissue chips. Otherwise, it can be understood that in window-closed position (window 120 of outer sleeve 112 closed by rotation of inner sleeve 122), the suction forces and fluid flows through the probe may be diminished until the window is again partly open. It should be appreciated that the number of holes 245 can range from one to 20 or more, and the sleeve 244 can be adapted to cover one or more holes with a tactile indication of the sleeve's position relative to the holes 245. Detents or other indicators can be provided in the outer sleeve 112 and sleeve 244 to allow the physician to observe or receive a signal indicating the number of holes 245 that are covered or uncovered.

In another variation, the controller 145 can have an algorithm adapted to energize and de-energize the electrodes (150, 175) on each revolution of the inner sleeve 122 in bore 168 of outer sleeve 112. More in particular, in the working end embodiment of FIGS. 2A-3, the electrodes 150, 175 are energized only as the leading edge 160a of inner sleeve 122 is exposed and advances past the edge of window 120 in outer sleeve 112. The electrodes are de-energized as leading edge 160a of inner sleeve 122 advances to a window-closed position. This aspect of the invention is advantageous because the electrode 150 has an opportunity to cool when the electrode is not resecting tissue and thus plasma cannot cause damage to the polymeric coating of either sleeve 112 or 122. The algorithm for energizing and de-energizing the electrodes 150, 175 is enabled by the sensor mechanism that determines rpm of the inner sleeve 122 as described above. The microswitch 196 as shown in FIG. 4 and controller 145 allows determination of the rotational position of the inner sleeve relative to window 120 on each revolution. Thus, the controller 145 can energize and de-energize the electrodes 150, 175 based on signals from the microswitch 196. In another variation, the controller can activate and de-activate the electrodes in response to measured electrical parameter relative to electrodes that will vary during each 360° rotation of the inner sleeve. For example, the electrical parameter can be impedance or capacitance.

In another embodiment, a tissue resecting probe can use signals from the microswitch 196 (FIG. 4) in combination with user inputs, for example the physician releasing a trigger or footswitch, to stop the inner sleeve rotationally relative to the outer sleeve in at least a first position or in multiple positions. In one example, the first position can comprise alignment of the outer and inner sleeve windows to provide a window-open configuration to prevent trapping of tissue. A second position can comprise non-alignment of the outer and inner sleeve windows to provide a partly window-open configuration, wherein the electrodes are configured in a position useful for coagulating tissue.

In another variation, the controller 145 can have an algorithm adapted to modulate negative pressure in the tissue extraction channel 146 upon each revolution of the inner sleeve 122 in bore 168 of outer sleeve 112. In one method, the negative pressure source 135 is actuated for the interval in which leading edge 160a of inner sleeve 122 is exposed and energized as the electrode 150 advances past the edge of window 120 in outer sleeve 112 and for the following 180° of rotation until leading edge 160a advances to a window-closed position. During the following 180° of rotation, the negative pressure source 135 can be turned off or can operate at a lower setting. This aspect of the invention allows for a high level of negative pressure for suctioning tissue into the window and a lower level of negative pressure at other times. In another variation, the higher level of negative pressure for suctioning tissue into the window can occur for an interval, for example 10° to 90° of rotation before the leading edge 160a of inner sleeve 122 is exposed and advances past the edge of window 120 in outer sleeve 112, again to suction tissue into the window.

Figure 9A:
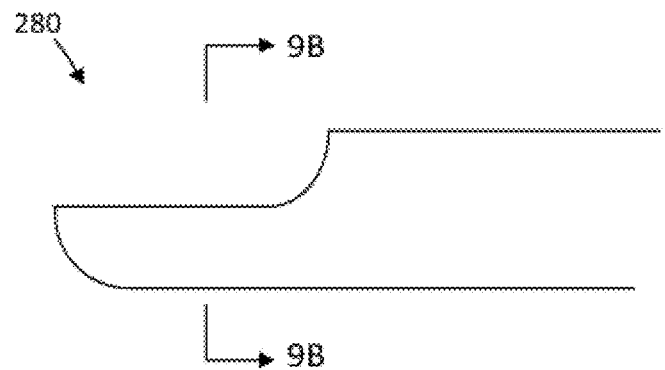
FIG. 9A is a side view of the distal end of the inner sleeve of an RF resecting probe similar to that of FIG. 2A.
Figure 9B:
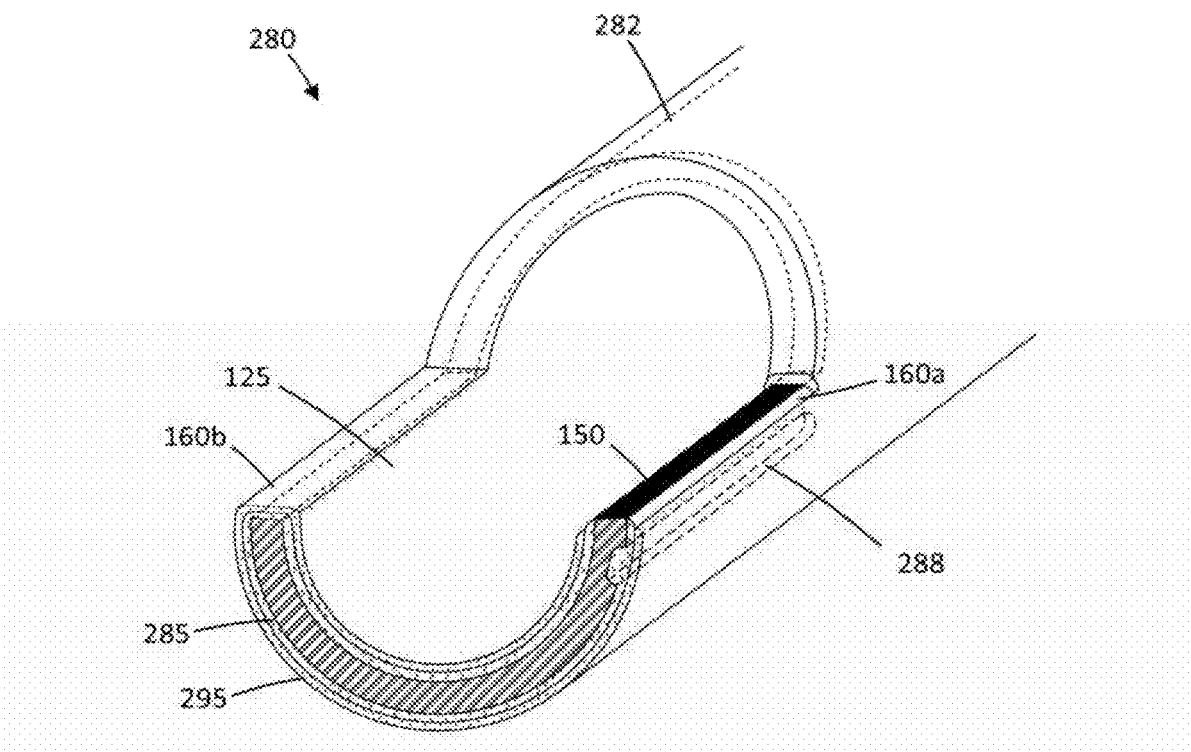
FIG. 9B is a partial sectional view of the inner sleeve of FIG. 9A taken along line 9B-9B of FIG. 9A.

FIGS. 9A-9B illustrate another variation of a distal end 280 of inner sleeve 282 with an asymmetric electrode similar to that of FIG. 7. The inner sleeve 282 of FIG. 9B is configured to rotate in an outer sleeve 112 of the type shown in FIG. 2B. This variation includes at least one layer of polymeric material, for example polymer 285, that extends up to leading edge 160a so that the electrode 150 comprises only the metal edge of the window 125. This differs from the embodiments of FIG. 2A and FIG. 7 in that such earlier variations had larger surface area electrodes 150 that extended around the sides and edge of the window 125. It has been found that an electrode 150 having a smaller surface area is advantageous for multiple reasons, for example, allowing for a lower power RF source 140 and for ease of initiating and maintaining plasma about the electrode 150 under varied fluid flow conditions around the working end during a procedure.

In FIG. 9B, it can be seen that polymer 285 extends around all inner and outer surfaces of sleeve 282 except for one edge of window 125 which thus comprises the electrode 150. As can be seen in FIG. 9B, the trailing edge 160b during rotation is covered in the polymer layer. The polymer 285 can be any material described above, and in one variation is a silicone having a durometer of Shore A 30 to 90. In one embodiment, the polymer 285 has a durometer of Shore A 60 to 70. In order to enhance adherence of polymer 285 to the metal sleeve 282, any undercut features, surface roughness, sand-blasting or the like can be used as described previously. In the variation depicted in FIG. 9B, a surface groove 288 is provided in metal sleeve 282 in at least one surface proximate the edge of window 125.

As a further optional feature, the variation of FIG. 9B shows a second layer of a polymer 295 that can be a polymer having lubricious characteristics and a higher durometer. Such a polymer 295 can be a Teflon or Parylene. Each of the polymers 285, 295 can have a thickness ranging from 0.001" to 0.010".

Figures 10A, 10B, 10C:
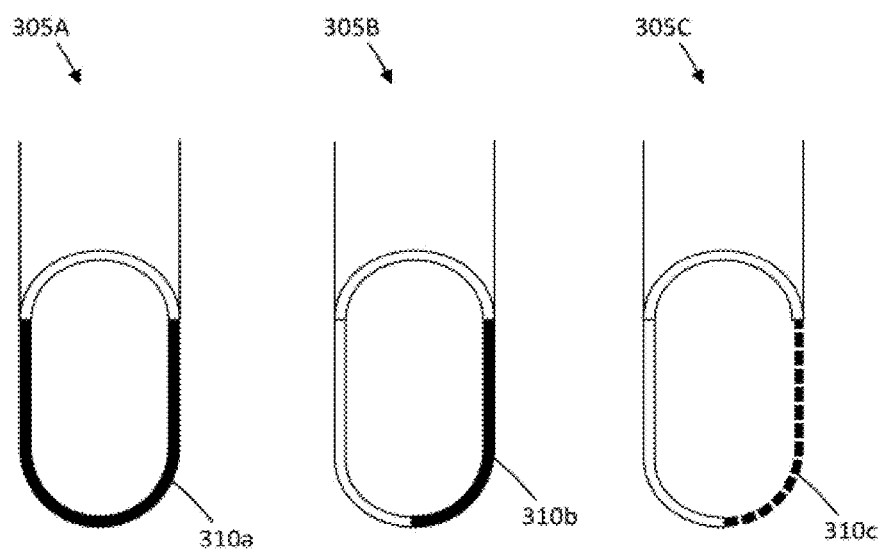
FIG. 10A is a schematic view of a distal end of another embodiment of inner sleeve of an electrosurgical cutting probe showing electrode surface area.
FIG. 10B is a schematic view of a distal end of another inner sleeve showing the surface area of an asymmetric electrode.
FIG. 10C is a schematic view of a distal end of another inner sleeve showing the surface area of a segmented asymmetric electrode.

In another aspect of the invention relating to FIGS. 9B and 10A-10C, the exposed surface area of electrodes in inner sleeve ends 305A, 305B and 305C are substantially small to permit instantaneous initiation of plasma under any fluid flow rates about the electrode with a given power supply. FIG. 10A illustrates an electrode 310a as a window edge only (see FIG. 9B) that is symmetrical around the window 125. FIG. 10B illustrates an electrode 310b that is asymmetric and exposed only around the leading edge 160a of window 125. FIG. 10C illustrates an electrode 310c that is asymmetric and segmented around leading edge to provide even less surface area. In general, the exposed surface area of an electrode (310a-310c) is less than 0.02 sq. inches, less than 0.01 sq. inches or less than 0.005 sq. inches.

What is claimed is:

1. A tissue-resecting probe comprising:
   an elongated probe comprising a windowed outer sleeve and cooperating windowed inner sleeve that is rotatable to resect tissue, wherein an edge of the inner sleeve window comprises a first polarity electrode and a portion of the outer sleeve comprises a second polarity electrode;
   a motor within a handle portion of the probe for rotating the inner sleeve;
   a slip coupling between a motor shaft and the inner sleeve, wherein the slip coupling is configured to slip if resistance to rotation of the inner sleeve exceeds a predetermined level; and
   a controller and electrical source for operating the motor and for energizing the electrodes, the controller including an algorithm for detecting electrical parameters of the motor indicative of slipping of the slip coupling.

2. The tissue-resecting probe of claim 1 wherein the slip coupling comprises at least one belt.

3. The tissue-resecting probe of claim 1 wherein the algorithm is further configured to de-energize the electrodes upon detection of slipping of the slip coupling.

4. A tissue-resecting probe comprising:
   an elongated probe comprising a windowed outer sleeve and cooperating windowed inner sleeve that is rotatable to resect tissue, wherein an edge of the inner sleeve window comprises a first polarity electrode and a portion of the outer sleeve comprises a second polarity electrode;
   a motor for moving the inner sleeve;
   an electrical source operatively connected to the first and second electrodes;
   a pressure source in communication with a passageway in the inner sleeve;
   a controller for controlling the motor, electrical source and pressure source, wherein the controller is configured to selectively provide negative pressure or positive pressure to the interior passageway, wherein the controller is configured to receive a signal of an operational parameter of the motor to select negative pressure or positive pressure.

5. The tissue-resecting probe of claim 4 wherein the controller is further configured to de-activate the first and second electrodes in response to a signal of an operational parameter of the motor.

6. The tissue-resecting probe of claim 4 wherein the controller is further configured to de-activate the first and second electrodes in response to a pressure signal from a pressure sensor.

7. A tissue-resecting probe comprising:
   an elongated probe comprising a windowed outer sleeve and cooperating windowed inner sleeve that is rotatable to resect tissue, wherein an edge of the inner sleeve window comprises a first polarity electrode and a portion of the outer sleeve comprises a second polarity electrode;
   a motor for moving the inner sleeve;
   an electrical source operatively connected to the first and second electrodes;
   a pressure source in communication with a passageway in the inner sleeve;
   a controller for controlling the motor, electrical source and pressure source, wherein the controller is configured to selectively provide negative pressure or positive pressure to the interior passageway, wherein the controller is configured to receive a pressure signal from a pressure sensor to select negative pressure or positive pressure.

8. A tissue-resecting probe comprising:
   an elongated probe comprising a windowed outer sleeve and cooperating windowed inner sleeve that is rotatable to resect tissue, wherein an edge of the inner sleeve window comprises a first polarity electrode and a portion of the outer sleeve comprises a second polarity electrode;
   a motor for moving the inner sleeve;
   an electrical source operatively connected to the first and second electrodes;
   a pressure source in communication with a passageway in the inner sleeve;
   a controller for controlling the motor, electrical source and pressure source, wherein the controller is configured to selectively provide negative pressure or positive pressure to the interior passageway, wherein the controller is configured to de-activate the first and second electrodes in response to selection of a negative pressure or positive pressure applied to the interior passageway.

* * * * *